US009381190B2

(12) United States Patent
McCarty

(10) Patent No.: US 9,381,190 B2
(45) Date of Patent: *Jul. 5, 2016

(54) MELATONIN TABLET AND METHODS OF PREPARATION AND USE

(71) Applicant: PHARMACEUTICAL PRODUCTIONS, INC., Miami Springs, FL (US)

(72) Inventor: John A. McCarty, Miami Springs, FL (US)

(73) Assignee: PHARMACEUTICAL PRODUCTIONS INC., Miami Springs, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,689

(22) Filed: Feb. 27, 2015

(65) Prior Publication Data

US 2015/0174101 A1    Jun. 25, 2015

Related U.S. Application Data

(63) Continuation of application No. 13/633,924, filed on Oct. 3, 2012, now Pat. No. 8,992,948, which is a continuation of application No. 12/595,183, filed as application No. PCT/US2008/004615 on Apr. 10, 2008, now abandoned.

(60) Provisional application No. 60/922,921, filed on Apr. 11, 2007.

(51) Int. Cl.
| *A61K 31/4045* | (2006.01) |
| *A61K 9/00* | (2006.01) |
| *A61K 9/20* | (2006.01) |
| *A61K 31/40* | (2006.01) |
| *A61K 31/70* | (2006.01) |
| *A61K 9/14* | (2006.01) |

(52) U.S. Cl.
CPC ........... *A61K 31/4045* (2013.01); *A61K 9/0056* (2013.01); *A61K 9/143* (2013.01); *A61K 9/2009* (2013.01); *A61K 9/2013* (2013.01); *A61K 9/2018* (2013.01); *A61K 9/2031* (2013.01); *A61K 9/2095* (2013.01); *A61K 31/40* (2013.01); *A61K 31/70* (2013.01)

(58) Field of Classification Search
CPC ... A61K 31/4045; A61K 31/40; A61K 31/70; A61K 9/0056; A61K 9/2009; A61K 9/2018; A61K 9/2031; A61K 9/143; A61K 9/2013; A61K 9/2095

See application file for complete search history.

(56) References Cited

U.S. PATENT DOCUMENTS

| 4,908,389 | A | 3/1990 | Mahjour et al. |
| 5,073,374 | A | 12/1991 | McCarty |
| 5,688,520 | A * | 11/1997 | Karsenty ............ A61K 31/4045 424/434 |
| 5,900,247 | A | 5/1999 | Rault |
| 6,242,004 | B1 | 6/2001 | Rault |
| 6,255,502 | B1 | 7/2001 | Penkler et al. |
| 8,992,948 | B2 * | 3/2015 | McCarty .............. A61K 9/0056 424/400 |
| 2003/0235596 | A1 * | 12/2003 | Gao ..................... A61K 9/1075 424/400 |
| 2014/0303227 | A1 * | 10/2014 | McCarty .............. A61K 9/2009 514/419 |

FOREIGN PATENT DOCUMENTS

| CN | 1488346 | * | 4/2004 | ......... A61K 31/4045 |
| WO | WO96/15782 | * | 5/1996 | ............. A61K 31/19 |
| WO | WO2004/075877 | * | 9/2004 | ............... A61K 9/00 |
| WO | WO2004075877 | | 9/2004 | |

OTHER PUBLICATIONS

Tao CN1488346 Machine Translation.*
"Colloidal Silicon Dioxide".*
Amir Shojaei, Buccal Mucosa as a Route for Systemic Drug Delivery: A Review, 1 J Pharm. Pharmaceut. Sci. 15, 18-20 (1998).
Yajaman Sudhakar, et al, Buccal Bioadhesive Drug Delivery—A Promising Option for Orally Less Efficient Drugs, 114 J Control. Rel. 15, 23-25 (2006).
Demuro et al. (2000) The Absolute Bioavailability of Oral Melatonin, J. Clin. Pharmacol., 40(7):781-784.
Hasenzahl et al., New Types of Fumed Silica (Colloidal Silicon Dioxide) toi Enhance Performance of Solid Dosage Forms, Degussa AG, Aerosil & Silanes Division, Research & Applied Technology Aerosil, marketing poster (1 page).
McCarthy et al., Using Porous Silicas in a 2-Step Mixing Process Improves Moisture Control, API Stability, Flow Properties, and Uniformity, GRACE marketing poster (1 page).
AAPS Annual Meeting and Exposition (2015), FLORITE, The Unique Excipient, Tomita Pharmaceuticals Co., Ltd., poster, 1 page.

* cited by examiner

*Primary Examiner* — Sean Basquill
(74) *Attorney, Agent, or Firm* — Ann-Louise Kerner; DLA Piper LLP (US)

(57) ABSTRACT

The present invention provides a pharmaceutical composition for sublingual or buccal administration of actives with low to poor aqueous solubility, e.g. the indole hormone melatonin, which contains a solution of the active in a pharmaceutically acceptable solvent adsorbed or absorbed onto particles of a pharmaceutically acceptable carrier and methods of preparing and using the pharmaceutical composition.

6 Claims, 2 Drawing Sheets

MELATONIN TABLET AND METHODS OF PREPARATION AND USE

CROSS-REFERENCE TO RELATED APPLICATIONS

This application is a continuation of U.S. patent application Ser. No. 13/633,924, filed on Oct. 3, 2012, now U.S. Pat. No. 8,992,948, which issued on Mar. 31, 2015, which is a continuation of U.S. patent application Ser. No. 12/595,183, filed on Oct. 8, 2009, and now abandoned, which is a National Stage application under 35 U.S.C. §371 and claims benefit under 35 U.S.C. §119(a) of International Application No. PCT/US2008/004615, filed on Apr. 10, 2008, which claims benefit of U.S. Provisional Patent Application No. 60/922,921, filed on Apr. 11, 2007, the disclosures of which are hereby incorporated by reference in their entireties.

BACKGROUND OF THE INVENTION

Hormones such as the indole hormone, melatonin, are widely distributed in both plant and animal sources. Melatonin can be found in human milk, bananas, beets, cucumbers, and tomatoes. Chemically, melatonin is N-acetyl-5-methoxytryptamine, a derivative of serotonin, which in turn is derived from tryptophan. Melatonin is a ubiquitous natural neurotransmitter-like compound produced primarily by the pineal gland, and is involved in numerous aspects of the biological and physiologic regulation of body functions.

See, e.g., Malhotra, S., et al., Medscape General Medicine 2004; 6(2), 46; and www.nlm.nih.gov/medlineplus/print/druginfo/natural/patient-melatonin.html for general discussion.

The role of endogenous melatonin in circadian rhythm disturbances and sleep disorders is well established. Some studies have shown that melatonin may also be effective in breast cancer, fibrocystic breast diseases, and colon cancer. Melatonin has been shown to modify immunity, the stress response, and certain aspects of the aging process; some studies have demonstrated improvements in sleep disturbances and "sundowning" in patients with Alzheimer's disease. The antioxidant role of melatonin may be of potential use for conditions in which oxidative stress is involved in the pathophysiologic processes. The multiplicity of actions and variety of biological effects of melatonin suggest the potential for a range of clinical and wellness-enhancing uses, especially considering that as one ages, the production of this key hormone goes into steady decline. Indeed, for an octogenarian, the amount produced is quite nominal.

Through melatonin release, the pineal gland maintains the internal clock governing the natural rhythms of body function. This apparent clock-setting property of melatonin has led to the suggestion that it is a "chronobiotic" substance that alters and potentially normalizes biological rhythms and adjusts the timing of other critical processes and biomolecules (hormones, neurotransmitters, etc.) that, in turn, exert numerous peripheral actions. The sleep-inducing effects of melatonin have advantages over conventional hypnotics, since melatonin, itself, is not a hypnotic drug. Melatonin only induces a natural state of sleepiness, and does not have the adverse side-effects of conventional hypnotics and prescription sleeping aids.

Melatonin has previously been used pharmaceutically, and has been prepared for oral administration (see, e.g., WO1995/003043). These preparations include melatonin formulated with a cyclodextrin (WO 1999/047175), and as a microemulsion (U.S. Pat. No. 5,362,745). However, as with most oral preparations, it can take more than 30 minutes after administration for the blood plasma concentration of melatonin to reach its peak. Goldberg, M J, Bergstrom, R F R, Smith, B P, Simcox, E A, Thomasson, H R, Shipley, L A: Sleep Research 1997: 26:101. This is due, in part, to the need for gastrointestinal absorption to occur before the melatonin is available in the bloodstream. Further, melatonin's oral bioavailability is poor and erratic. Melatonin's absolute oral bioavailability has been shown to be approximately 15% and peak plasma concentrations can vary over 20 fold range. DeMuro R L, Nafziger A N, Blask D E, Menhinick A M, Bertino J S: Journal of Clinical Pharmacology 2000: 40; 781; Di W L, Kadva A, Johnston A, Silman R: New England Journal of Medcine 1997: 336; vol. 14, 1028. Thus, oral administration of melatonin in currently available preparations does not provide for rapid onset of action, and its poor and erratic GI absorption make it an unsuitable route of administration.

Several sublingual, buccal, orally dissolving tablets and films containing melatonin are also available commercially. For example, transmucosal formulations are described in WO 1996/030013 and U.S. Pat. No. 5,688,520. However, in these formulations, melatonin is compounded in its undissolved, or solid, state. For any drug to be absorbed into the bloodstream, it must be dissolved, i.e., in solution. Due to melatonin's poor water solubility much of the dosage from a currently available preparation is swallowed undissolved in the saliva, leading to poor and erratic absorption in the GI tract. Accordingly, hormone drugs such as melatonin having low to poor water solubility, are expected to be poorly suited for buccal or sublingual administration.

Other routes of administration for melatonin, including nasal and oral sprays have been considered. U.S. Pat. No. 6,007,834. However, sprays are less desirable because of inherent compliance issues such as improper manipulation of the actuator, swallowing of the dosage before dissolution of the drug, and the restrictions on usage when the patient has sinus congestion or a head cold. This again leads to erratic and poor melatonin bioavailability. Therefore sprays are not the optimal route for routine melatonin administration.

Accordingly, there is a need in the medical and pharmaceutical arts to provide an oral dosage form, preferably for sublingual or buccal administration, wherein the subject dosage form can provide rapid and consistent delivery of a hormone having low to poor water solubility, such as melatonin. This need is met by the subject composition, as well as its method of preparation and administration. The subject melatonin formulation can advantageously be useful to administer the drug to a patient in significantly less time and with more consistent and higher bioavailability than previously available dosage forms. Therefore, this invention as claimed, provides a unique composition, delivery system and method of administration for melatonin and other hormones having low to poor water solubility.

SUMMARY OF THE INVENTION

The present invention provides a pharmaceutical composition for sublingual or buccal administration of a hormone, e.g., melatonin, having relatively low to poor solubility in water or other aqueous solutions. The composition comprises the hormone in association with an inactive carrier, wherein the hormone is preferably absorbed or adsorbed onto the carrier, and thereafter formed into a solid dosage form such as a tablet. The carrier used in the subject composition is preferably a pharmaceutically acceptable carrier provided as a bead, a granule, a particle, or the like. Uniquely, the composition according to the subject invention comprises a pharmaceutically acceptable solvent in which the hormone is dissolved and maintained in a solubilized state in the final solid dosage form.

For purposes of the subject invention, it would be understood that the term "melatonin" is a specific hormone having low to poor water solubility. Melatonin is preferably used as the active ingredient in compositions of the invention. It would also be understood that use of the term melatonin refers to other hormone active ingredients having low to poor water solubility, such as estrogens, progesterone, testosterone, and dihydrotestosterone. Accordingly, embodiments of the subject invention include compositions wherein an estrogen, progesterone, testosterone, or dihydrotestosterone, or combinations thereof, are substituted for or used with melatonin. It would also be understood that these hormones may be in their respective derivative form. Therefore, reference to melatonin, estrogens, progesterone, testosterone, or dihydrotestosterone includes any salt, prodrug, metabolite, isomer, or derivative thereof having low to poor water or aqueous solubility.

In accordance with certain embodiments of the present invention, the composition comprises a pharmaceutically acceptable carrier selected from silica, microcrystalline cellulose, cellulose, silicified microcrystalline cellulose, clay, talc, starch, pregelatinized starch, calcium carbonate, calcium silicate, dicalcium phosphate, magnesium carbonate and mixtures thereof. These carriers are well known in the pharmaceutical arts as being suitable for forming particles, such as beads, pellets and granules using conventional methods of preparation. For purposes of the subject invention, the term "particle" encompasses, and means, and is used interchangeably with, "carrier," "bead," "pellet," "granule" or any other particle-like form as well-recognized and accepted in the pharmaceutical arts. In a preferred embodiment, the pharmaceutically acceptable carrier is silica, which is also called colloidal silicon dioxide. In certain preferred embodiments, the carrier has a particle size ranging from about 3 microns to about 30 microns.

In certain embodiments, the pharmaceutically acceptable solvent used for dissolving the melatonin and forming the melatonin-containing solution for associating the melatonin with the carrier particle is selected from polyethylene glycol, ethanol, ethyl acetate, isopropyl alcohol, triacetin, triethyl citrate.tributyl citrate, substituted polyethylene glycols, propylene glycol, bisabolol. glycerin, mineral oil, oleic acid, oleyl alcohol, ethyl oleate, fatty acid esters, squalane. animal oils, vegetable oils, hydrogenated vegetable oils, isopropyl myristate. isopropyl palmitate, glycofurol, terpenes, essential oils, alcohols, water, polyols, silicone fluids, and/or glycerides and mixtures thereof.

A preferred pharmaceutically acceptable solvent is polyethylene glycol and a mixture of polyethylene glycol and oleic acid. It would be understood that the solution may be formed from an aqueous or non-aqueous solvent or a mixture thereof, and may be formed from a volatile and a non-volatile solvent, or a mixture thereof, so long as the melatonin or other hormone having low to poor water solubility is in solution when coated, adsorbed or absorbed onto the carrier. In an embodiment employing a volatile solvent, such volatile solvent is preferably removed, e.g., by drying, after coating, adsorption, or absorption.

The concentration of active ingredient, such as melatonin, in the solvent is preferably in the range of about 5% to about 30% and more preferred 10% to 20%. The preferred weight: weight ratio of carrier:solution being in the range of about 1:0.5 to about 1:4 and more preferred 1:1 to 1:2. In certain embodiments, the pharmaceutical composition contains from about 0.01 to about 3 mg of melatonin per unit dose and more preferred 0.5 to 2 mg.

The pharmaceutical composition of the subject invention may further comprise a diluent, a disintegrant, a lubricant, or other excipient as would be readily understood in the pharmaceutical arts for preparation of a final dosage form as desired. For example, in order to prepare a solid dosage form such as a compressed tablet, excipients well known in the tableting arts can be employed in a manner consistent with such known tableting techniques and procedures to form a compressed dosage form such as a compressed tablet.

Preferably, the pharmaceutical composition of the subject invention is provided as a unit dose form, and more preferably as a solid dosage form, such as a compressed tablet, for buccal or sublingual administration. A most preferred embodiment of the subject invention comprises a tablet which provides rapid administration of the API upon sublingual or buccal administration of the composition.

The composition of the subject invention advantageously provides the active ingredient, e.g., a hormone such as melatonin having relatively low to poor solubility in aqueous solvents, in a dissolved form. Being in a dissolved form, the melatonin can be directly absorbed into the bloodstream through the oral mucosa, without having to be dissolved by the aqueous environment provided by saliva in the mouth or in the gastrointestinal tract. A further advantage of the drug delivery system of the subject invention includes enhanced oral mucosal absorption of the active provided in the composition because less drug is swallowed as undissolved drug released from the dosage form. Accordingly, this drug delivery system provides for rapid onset of drug action with higher and more consistent bioavailability.

The present invention also provides a process for the preparation of a pharmaceutical composition as described above, which involves dissolving a hormone having low to poor aqueous solubility, such as melatonin, in a pharmaceutically acceptable non-aqueous solvent to form a drug solution, mixing the solution with particles of a pharmaceutically acceptable carrier to afford coating, absorption or adsorption onto the particles, and then, if desired, mixing the adsorbed or absorbed particle's with other ingredients, e.g., the pharmaceutically acceptable excipients, to form the final composition. In certain embodiments, the solution is mixed with the particles to provide a flowable powder that can be compounded or compressed into a solid dosage form or can be combined with other or additional compressible materials to facilitate compression of the composition into a solid, unitary dosage form. The process can further comprise the step of compressing the composition to form tablets.

The present invention further provides a method of providing a patient with melatonin therapy, comprising the steps of providing a composition in accordance with the subject invention, administering the composition by a sublingual or buccal route to a patient in need of treatment with melatonin.

DETAILED DESCRIPTION

Figure 1:
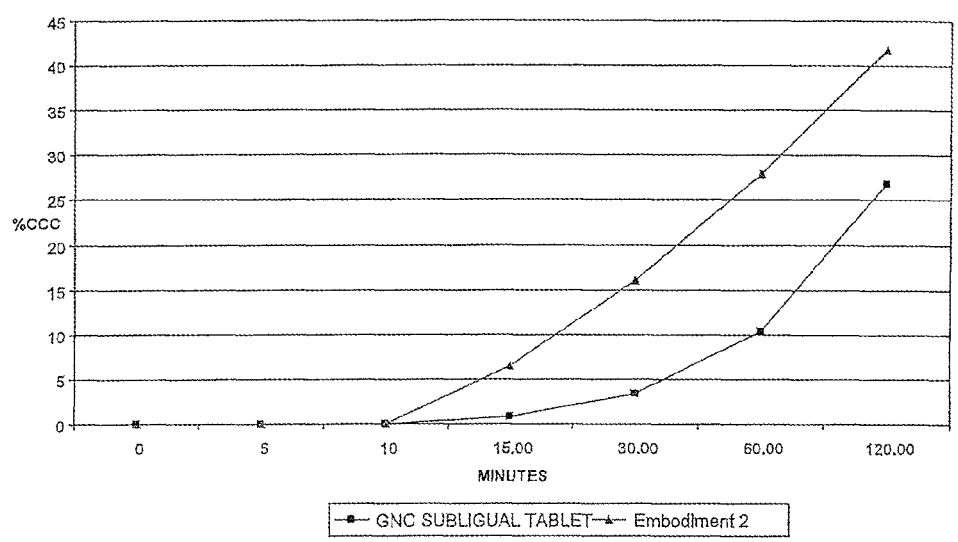
FIG. 1 shows the comparative buccal flux using a 1 mg melatonin tablet made in accordance with Example 2 of the present invention versus a commercially available sublingual melatonin tablet.
Figure 2:
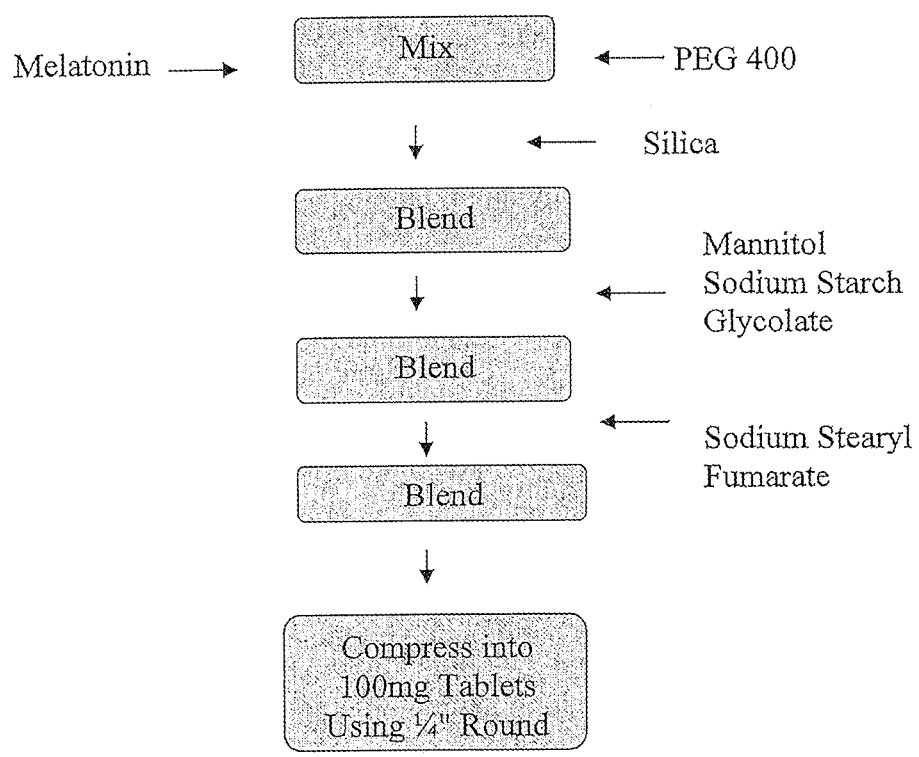
FIG. 2 is a flow chart showing steps comprising the manufacture of a sublingual tablet containing a dose of 1 mg melatonin.

This invention relates to a pharmaceutical composition for sublingual or buccal administration of a hormone having low to poor aqueous solubility, such as melatonin. For purposes of the subject invention, the description refers to melatonin as the active pharmaceutical ingredient (API), or drug, but would be understood by persons having ordinary skill in the art to include other hormones which have low to poor water solubility in aqueous environment or in aqueous biological fluids such as saliva or gastrointestinal fluids. The invention further relates to a method of manufacture for the sublingual or buccal dosage form and use of the subject preparation for sublingual or buccal melatonin delivery and treatment of patients in need of melatonin therapy.

This invention relates to a novel delivery system of a drug, such as melatonin, providing a unique mechanism to enhance delivery of the drug. This unique system is designed to deliver melatonin through the buccal or sublingual mucosa and directly into systemic circulation. This is unlike any of the currently marketed sublingual or buccal products containing a hormone, such as melatonin, because those marketed products are formulated in a solid form, such as an emulsion or solid dispersion, so that much of the melatonin is incompletely dissolved in the local buccal or sublingual delivery area. Those marketed products disintegrate in the mouth or are chewed in order to release the melatonin from the dosage form, causing the undissolved melatonin to be swallowed and absorbed in the gastrointestinal tract, and thereby leading to poor and erratic bioavailability for the released drug.

Melatonin is poorly soluble in water or other aqueous biological fluids and, when delivered in a undissolved state, as in the currently available melatonin products, the drug remains undissolved in saliva and must therefore be swallowed in order to be absorbed in any substantial amount. Thus, for these products, the onset of action, absorption and first pass metabolism are no different than from swallowing an immediate-release oral tablet or capsule containing undissolved melatonin. Such tablets are considered to be immediate-release only due to the rapid disentegration of the dosage form. These available tablets release melaoning in an undissolved state, and drug absorption is limited by how quickly the drug dissolves in the local delivery area.

Unlike other sublingual tablets and orally disentegrating tablets, where melatonin must first dissolve into the saliva to be absorbed, the subject invention advantageously provides the active drug, e.g., a hormone such as melatonin having low to poor water or aueous solubility, already in solution as present in the final dosage form. In the subject invention, the hormone such as melatonin is not provided as an emulsion or solid dispersion, but is completely dissolved and in solution. Therefore melatonin sublingual/buccal delivery is enhanced by this invention, because melatonin does not have to dissolve in the saliva before being absorbed. Further, by being formulated into a small rapidly disintegrating tablet the area for absorption is localized around the disentegrating tablet. Having the drug solubilized and contained to a local delivery site keeps the drug in solution, and thus having high thermodynamic activity which enhances transmucosal absorption. The rapid onset of melatonin action from the delivery system provided by the subject invention can provide for rapid drug absorption, resulting in drug plasma pharmacokenetics more similar to an intravenous injection, with none of the vicissitudes associated with gastrointestinal (GI) administration, e.g., poor absorption, erratic absorption, first pass metabolism, food and dietary supplements effects on oral bioavailability.

A sublingual/buccal dosage form, e.g., a tablet, in accordance with the subject invention can enhance delivery of drug with poor aqueous solubility, such as melatonin, by sublingual or buccal administration by providing the drug in solution, or in a dissolved state, within a solid dosage form designed for localized drug delivery and absorption.

The melatonin sublingual tablets as embodied in this invention preferably range from 50 to 150 mg total tablet weight depending on the dosage. In vitro drug dissolution testing from rapid release formulations is substantially complete within 15 minutes and the tablet disintegrates under the tongue typically within a few minutes, preferably less than 5 minutes, more preferably within one to three minutes, and most preferably within 30 seconds to about two minutes. Thus onset of sleepiness from administering this sublingual tablet occurs form about 5-25 minutes, and preferably, within about 15 minutes, providing a rapid rise in melatonin plasma levels and reaching therapeutic levels or maximum concentration from the dosage form within these time periods.

A slower drug release can alternatively be formulated into the tablet, such as the addition of a slow-release coating, inclusion of pore-formers into the coating or core, incorporation of a matrix formulation, or the like, as are recognized in the art, to mimic a slow infusion using controlled release formulation methods. Thus, because the drug's dissolution rate is not a rate-limiting step in the delivery of drug to the patient, the delivery and absorption of drug to the patient can be predictably controlled by manipulation of the disintegration of the dosage form.

Preferred pharmaceutical compositions in accordance with the present invention can be formulated to provide a single dose of active ingredient, e.g., melatonin, between 0.01 mg to 3 mg and, preferably, of between 0.2 and 2.0 mg. When used in such low doses, compositions in accordance with the invention can advantageously provide consistent and sufficiently high peak melatonin blood plasma concentration ($C_{max}$), soon after administration to be effective in the treatment of human disease, particularly insomnia, or in causing drowsiness or sleep in humans. Thus, the present invention allows for consistently effective melatonin blood plasma concentrations to be achieved even when using lower melatonin doses than administered in currently available products.

In an embodiment of the invention, melatonin is dissolved in polyethylene glycol (PEG), e.g., PEG 400, PEG 200, PEG 300, PEG 600, or other suitable solvents include other molecular weight grades of PEG, ethanol, ethyl acetate, isopropyl alcohol, triacetin, triethyl citrate, tributyl citrate, substituted polyethylene glycols, propylene glycol, bisabolol, glycerin, mineral oil, ethyl oleate, oleic acid, oleyl alcohol, fatty acid esters, squalane, animal oils, vegetable oils, hydrogenated vegetable oils, isopropyl myristate, isopropyl palmitate, glycofurol, terpenes, essential oils, alcohols, polyols, silicone fluids, and/or glycerides and combinations of such solvents.

In order to convert the liquid melatonin solution into a flowable powder suitable for use in direct compression tableting requires the use of an adsorbent/absorbent carrier, such as silica (ZEOPHARM 5170, AEROPERL 300, SYLOID 244FP, SYLOID 63FP, SYLOID 72 FP, SIPERNAT 160PQ, SIPERNAT 50, SIPERNAT 50S, SIPERNAT 500LS, SIPERNAT 2200, SIDENT 8, SIDENT 9, SIDENT 10, SIDENT 22S) In certain embodiments, the carrier according the invention may also be microcrystalline celluloses, cellulose powder, silicified microcrystalline celluloses (PROSOLV 50, PROSOLV 90HD), silicas, clays, talcs, starches, pregelatinized starches, calcium carbonates, calcium silicates, cyclodextrins, dicalcium phosphates, and magnesium carbonates or combinations thereof.

In order to manufacture a rapidly disintegrating, directly compressible sublingual tablet other excipients can be used. For example, the diluent may be the water-soluble, direct compression tableting excipient, mannitol. Other water-soluble excipient according to the invention are one or more of the following: sugars, polyols, saccharides, polysaccharides, dextrate, dextrins, dextrose, fructose (ADVANTOSE FS 95), lactitol (FINLAC DC), lactose, erythritol, maltose, maltitol, maltodextrins, polydextroses, trehalose, mannitol (PEARLITOL 300 DC, PEARLITOL 400 DC, PEARLITOL 500 DC, MANNOGEM 2080, MANNOGEM EZ, PARTEK M200, PARTEK M300), polyethylene glycols, isomalts, sorbitol, sucrose and xylitol (XYLITOL 200. XYLITOL 300). A disintegrant can also be included to formulate a rapid breaking apart of the tablet following administration. An exemplary disintegrant is sodium starch glycolate. An exemplary tablet lubricant is sodium stearyl fumarate.

In an embodiment, other excipients, chosen to enhance processability, form, function or aesthetic appeal of the formulation can be included in a composition according to the invention. In such an embodiment, other excipients according to the invention is a buffering agent (such as phosphate, carbonate, tartrate, borate, citrate, acetate, and maleate buffers), colorant, flavoring, solvent and co-solvent, coating agent, binder, diluent, carrier, disintegrant, glidant, lubricant, opacifying agent, humectant, granulating agent, gelling agent, polishing agent, suspending agent, sweetening agent, anti-adherent, preservative, emulsifying agent, antioxidant, levigating agent, plasticizer, surfactant, tonicity agent, viscosity agent, enteric agent and coating, controlled-release agent and coating, wax, wetting agent, thickening agent, suppository base, stifling agent, stabilizing agent, solubilizing agent, sequestering agent, bioadhesive, ointment base, oleaginous vehicle, film-forming agent, essential oil, emollient, dissolution enhancer, dispersing agent, and/or cryoprotectant or combinations thereof.

EXAMPLE 1

In one embodiment, the invention provides a 1 mg strength melatonin sublingual/buccal tablet having a total tablet weight of about 100 mg, wherein the tablet comprises drug, an absorbent/adsorbent particulate carrier, such as silica; a diluent, such as mannitol; a disintegrant, such as sodium starch glycolate; and a lubricant, such as sodium stearyl fumarate, to facilitate tableting. In such an embodiment, melatonin is dissolved in PEG 400. The melatonin-in-PEG 400 solution is then processed into a into a flowable powder suitable for use in direct compression tableting. An exemplary formulation in accordance with the described formulation of this embodiment is provided in Table I, below.

TABLE I 1 mg Melatonin Sublingual/Buccal Tablet Formulation

| INGREDIENT | AMOUNT (mg/tablet) |
|---|---|
| Melatonin | 1.00 |
| Polyethylene glycol 400 | 7.00 |
| Silica | 4.50 |
| Mannitol | 84.00 |
| Sodium Starch Glycolate | 3.00 |
| Sodium Stearyl Fumarate | 0.50 |
| Total Tablet Weight | 100.00 |

EXAMPLE 2

In one embodiment, the invention provided a 1 mg strength melatonin sublingual/buccal tablet having a total tablet weight of about 68 mg. In this second exemplary embodiment, melatonin is dissolved in a mixture of solvents, PEG 400 and oleic acid. In order to convert the melatonin PEG 400/Oleic Acid solution into a flowable powder suitable for use in direct compression tableting, an adsorbent/absorbent particulate carrier, such as silica, can be used as above in Example 1. A tablet diluent, such as mannitol can be used for formulating a directly compressible tablet. Sodium starch glycolate was used as a disintegrant, and sodium stearyl fumarate was usd as a lubricant.

An exemplary formulation manufactured for this embodiment in accordance with the subject invention are provided in Table II, below.

TABLE II 1 mg Melatonin Sublingual/Buccal Tablet Formulation

| INGREDIENT | AMOUNT (mg/tablet) |
|---|---|
| Melatonin | 1.00 |
| Polyethylene glycol 400 | 5.00 |
| Oleic Acid | 1.30 |
| Silica | 5.00 |
| Mannitol | 52.30 |
| Sodium Starch Glycolate | 2.04 |
| Sodium Stearyl Fumarate | 1.36 |
| Total Tablet Weight | 68.00 |

EXAMPLE 3

An in vitro buccal skin flux study was conducted comparing melatonin permeation through buccal tissue culture from two 1 mg sublingual melatonin tablets having a formulation according to Example 2, against a commercially available sublingual tablet which does not include dissolved melatonin in the final dosage form. As shown in FIG. 1, the amount of melatonin that permeated the tissue was more than 3-fold greater after 30 minutes from a tablet of the subject formulation compared to a commercial GNC 1 mg melatonin sublingual tablet, as measured as percent label concentration (% LC). This shows enhanced rate of buccal tissue permeation of the invention as compared to a currently marketed sublingual melatonin tablet, which suggests a faster onset of action and greater bioavailability for the subject tablets in vivo. Therefore, it may be concluded that the onset of sleepiness would be much faster using a formulation in accordance with the subject invention, such as the formulation provided in Example 2.

EXAMPLE 4

A method of manufacture for a tablet according to an embodiment of the subject invention for sublingual/buccal administration may employ any suitable method known in the art including, but not limited to, the addition of the melatonin solvate to premanufactured tablets, cold compressions with inert fillers and binders, direct tablet compression blends, direct powder blends, wet or dry granulations, molding, lyophilization, microencapsulation, freeze drying, spray-congealing, spray-drying, co-melt, spheronization, triturates, troching, powder layering, pelleting, encapsulation. An exemplary method for the manufacture of a direct compression tablet of the formulation given in Example 1 is outlined step-wise, below and is schematically diagrammed in FIG. 1.

Embodiment 1

STEP 1: Mix melatonin and PEG 400 together to form a solution.

STEP 2: Blend the melatonin PEG 400 solution from Step 1 with silica until homogeneous to form a silica carrier blend.

STEP 3: Add the silica carrier blend from Step 2 to mannitol and sodium starch glycolate and mix until homogeneous to foam a further blend.

STEP 4: Add sodium stearyl fumarate to the further blend from Step 3 and blend until well lubricated to form a lubricated blend.

STEP 5: Compressing the lubricated blend from Step 4 into 100 mg tablets using ¼ inch round tooling.

Method of packaging. The sublingual/buccal tablets may be packaged in such a manner as to aid in maintaining stability. Packaging methods and materials may include, but are not limited to, blister packaging in a foil/foil, foil/Acrylonitrile, foil/Polychlorotrifluoroethylene laminates for blister packaging or glass and plastic bottles.

Method of Use: In an embodiment, a rapid onset of action melatonin buccal/sublingual tablet formulation with consistent bioavailability according to the invention is useful in the treatment of in circadian rhythm disturbances and sleep disorders is well understood. Some studies have shown that melatonin may also be effective in breast cancer, fibrocystic breast diseases, and colon cancer. Melatonin has been shown to modify immunity, the stress response, and certain aspects of the aging process: some studies have demonstrated improvements in sleep disturbances and "sundowning" in patients with Alzheimer's disease. The antioxidant role of melatonin may be of potential use for conditions in which oxidative stress is involved in the pathophysiologic processes. Since endogenous melatonin production declines with age, use of melatonin as a hormone replacement therapy or nutritional supplement is indicated. Accordingly, this invention is useful for all the above mention therapies. The typically treatment regiment starts by placing a melatonin sublingual tablet under the tongue and leaving it undistributed until dissolved, typically within 5 minutes. This can be supplemented with additional tablets as needed. The dosage range for this embodiment may vary from 0.01 to 3.0 mg depending on the therapeutic need.

The invention has been described with reference to various specific and preferred embodiments and techniques. However, it should be understood that many variations and modifications may be made while remaining within the spirit and scope of the invention.

What is claimed is:

1. A tablet for sublingual or buccal administration of melatonin, said tablet comprising:
    melatonin in a dissolved state;
    a solvent which is polyethylene glycol (PEG) 200, 300, 400, and or 600; and
    a pharmaceutically acceptable carrier to which the dissolved melatonin is adsorbed and which becomes a flowable powder, the carrier being silica or calcium silicate;
    where in melatonin is in a dissolved state in the tablet, and wherein the drug dissolution from the tablet is substantially complete within 15 minutes.

2. The tablet of claim 1, in which the concentration of melatonin solubilized in the solvent is in the range of about 5% w/w to about 30% w/w.

3. The tablet of claim 1, wherein the weight:weight ratio of carrier to melatonin solution is in the range of about 1:0.5 to about 1:4.

4. The tablet of claim 1, further comprising a diluent, a disintegrant, and/or a lubricant.

5. A process for the preparation of the tablet of claim 1, comprising the steps of:
    dissolving melatonin in the PEG to form a drug solution; and
    mixing the drug solution with the pharmaceutically acceptable carrier silica or calcium silicate to adsorb said solution to the carrier particles forming a flowable powder; and
    compressing the solution-adsorbed carrier particles into a tablet.

6. The process of claim 5, further comprising adding additional excipients to the solvated melatonin/adsorbent before compressing the solvated, adsorbed melatonin/adsorbent particles into the form of a tablet.

* * * * *